United States Patent
Sommer et al.

(10) Patent No.: US 8,329,016 B1
(45) Date of Patent: Dec. 11, 2012

(54) MICROFLUIDIC DEVICE HAVING AN IMMOBILIZED PH GRADIENT AND PAGE GELS FOR PROTEIN SEPARATION AND ANALYSIS

(75) Inventors: Gregory J. Sommer, Livermore, CA (US); Anson V. Hatch, Tracy, CA (US); Anup K. Singh, Danville, CA (US); Ying-Chih Wang, Pleasanton, CA (US)

(73) Assignee: Sandia Corporation, Albuquerque, NM (US)

( * ) Notice: Subject to any disclaimer, the term of this patent is extended or adjusted under 35 U.S.C. 154(b) by 560 days.

(21) Appl. No.: 12/551,047

(22) Filed: Aug. 31, 2009

Related U.S. Application Data

(63) Continuation-in-part of application No. 12/182,755, filed on Jul. 30, 2008.

(60) Provisional application No. 60/962,663, filed on Jul. 30, 2007.

(51) Int. Cl.
*G01N 27/453* (2006.01)

(52) U.S. Cl. ........................ 204/605; 204/644

(58) Field of Classification Search .......... 204/600–605, 204/644
See application file for complete search history.

(56) References Cited

OTHER PUBLICATIONS

Das, C., et al. "Integration of isoelectric focusing with multi-channel gel electrophoresis by using microfluidic pseudo-valves", Lab on a Chip, vol. 7, 2007, pp. 1806-1812.*
Sommer, G. J., et al. "On-chip isoelectric focusing using photopolymerized immobilized pH gradients", Analytical Chemistry, vol. 80, No. 9, May 1, 2008, pp. 3327-3333.*

* cited by examiner

*Primary Examiner* — J. Christopher Ball
(74) *Attorney, Agent, or Firm* — Timothy P. Evans

(57) ABSTRACT

Disclosed is a novel microfluidic device enabling on-chip implementation of a two-dimensional separation methodology. Previously disclosed microscale immobilized pH gradients (IPG) are combined with perpendicular polyacrylamide gel electrophoresis (PAGE) microchannels to achieve orthogonal separations of biological samples. Device modifications enable inclusion of sodium dodecyl sulfate (SDS) in the second dimension. The device can be fabricated to use either continuous IPG gels, or the microscale isoelectric fractionation membranes we have also previously disclosed, for the first dimension. The invention represents the first all-gel two-dimensional separation microdevice, with significantly higher resolution power over existing devices.

15 Claims, 15 Drawing Sheets

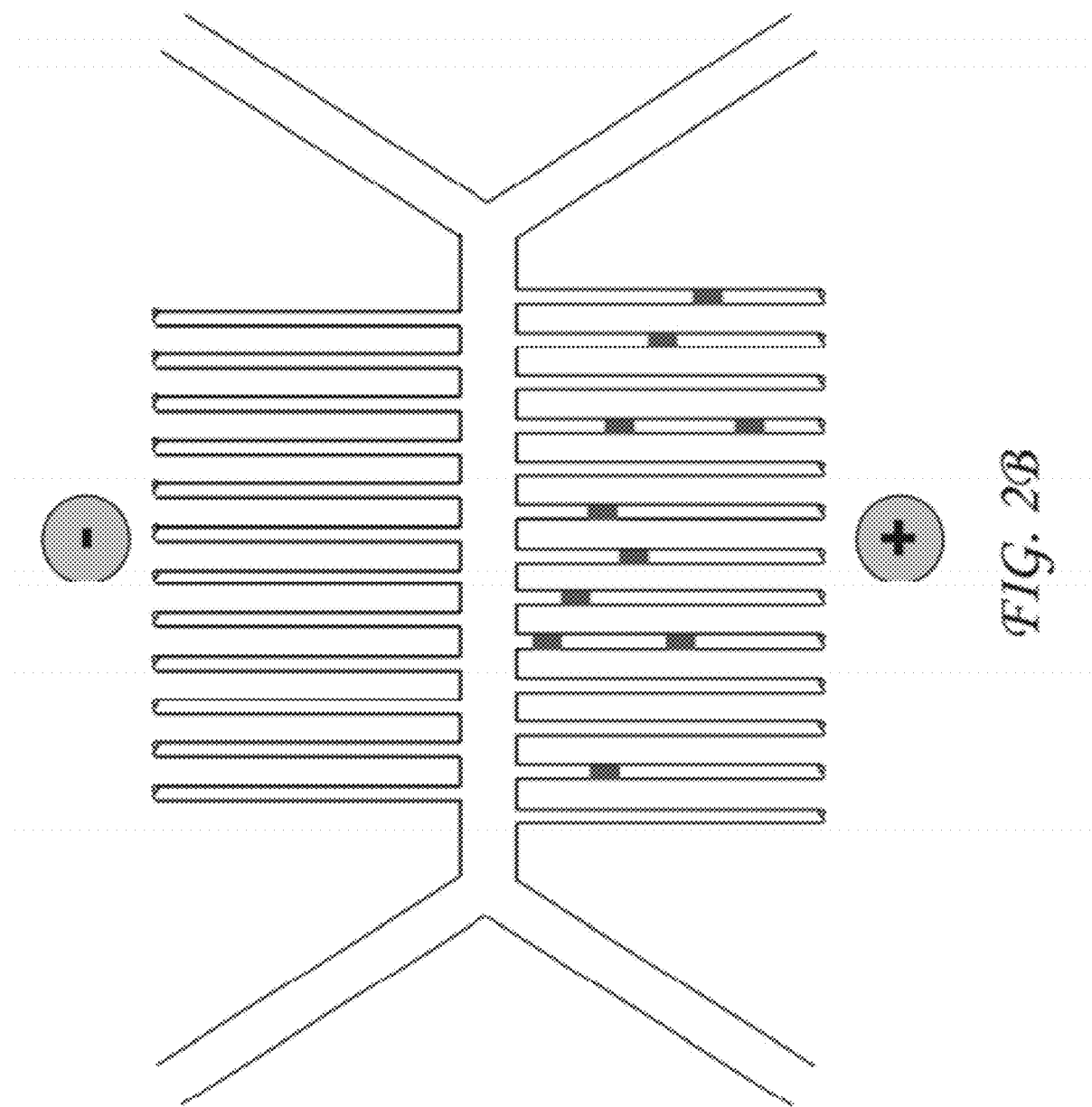

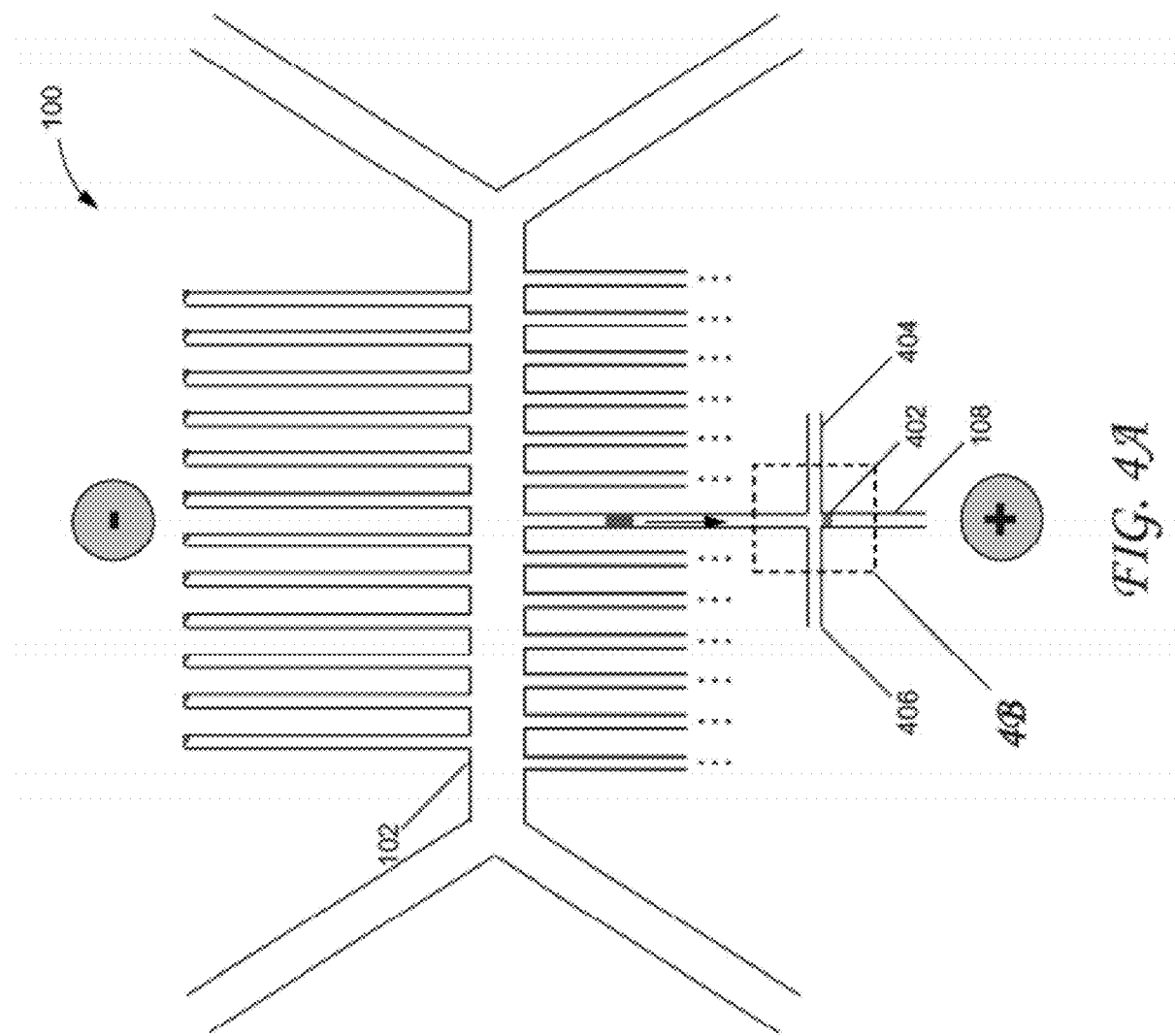

MICROFLUIDIC DEVICE HAVING AN IMMOBILIZED PH GRADIENT AND PAGE GELS FOR PROTEIN SEPARATION AND ANALYSIS

CROSS-REFERENCE TO RELATED APPLICATIONS

This application is a continuation-in-part of U.S. patent application Ser. No. 12/182,755 filed Jul. 30, 2008 that claims the benefit of U.S. Provisional Application No. 60/962,663 filed Jul. 30, 2007, and U.S. patent application Ser. No. 12/243,817 filed Oct. 1, 2008, the entire disclosures of which are incorporated by reference in their entirety.

STATEMENT OF GOVERNMENT SUPPORT

The United States Government has a paid-up license in this invention and the right in limited circumstances to require the patent owner to license others on reasonable terms as provided for by the terms of contract No. DE-AC04-94AL85000 awarded by the U.S. Department of Energy to Sandia Corporation.

BACKGROUND OF THE RELATED ART

1. Field of the Invention

The present invention generally relates to an integrated, miniaturized 2-D IEF/PAGE analysis device provided in a microfluidic format. This invention further provides separation dimensions (IEF and PAGE) in a continuous gel format. More particularly, the invention provides a first dimension having an immobilized pH gradient for rapid and high resolution isoelectric focusing (IEF), and a second dimension having a plurality of microchannels for polyacrylamide gel electrophoresis (PAGE). The invention also provides a means for introducing an anionic surfactant such as sodium dodecyl sulfate (SDS) into the second dimension.

2. Background and Related Art

One of the most reliable separation techniques used in proteomics involves combining isoelectric focusing with polyacrylamide gel electrophoresis (IEF-PAGE). Samples are first separated based on their isoelectric points along an established pH gradient, then separated orthogonally by their molecular weight through a size-exclusion polyacrylamide gel. The result is a high resolution two-dimensional fractionation of all species in the sample. The total peak capacity for a 2-D separation mechanism is the product of the peak capacities of each dimension, thereby significantly enhancing the assay resolving power: $n_{total}=n_1 n_2$. Conventional IEF-PAGE methodology involves using 7-18 cm-long immobilized pH gradient (IPG) strips for the first dimension, then transferring the strip to a slab gel for subsequent size-based elution. An anionic surfactant such as sodium dodecyl sulfate (SDS) is often included in the second dimension to enhance resolution by ensuring that all proteins obtain a constant charge/mass ratio. Unfortunately these assays are considerably labor-intensive and time-consuming, wherein the typical run time for a complete 2-D analysis can exceed 36 hours.

It will be appreciated that there has existed a long-felt need to miniaturize the 2-D IEF/PAGE process and incorporate it into a microfluidic format. Current techniques for deploying 2-D separation rely on handling bulk polymer gel slabs and/or performing a first separation process with one device and then moving the output of this first process to a second device for performing a second separation process (see U.S. Pat. Nos. 7,517,442, 6,969,452, and 6,013,165 and Published U.S. Application Serial Numbers 2002/0153252 and 2002/0033336). No one, however, has yet to provide a means for creating such gradients in microfluidic devices. Current methods suffer from several drawbacks, including complex instrumentation requirements, lack of temporal stability, and bulk flow along or perpendicular to the established gradient.

implementation of IEF and PAGE methodology into a microfluidic format provides several advantages over conventional approaches, such as: 1) reduced run times due to shorter length scales, 2) reduced sample volume requirements, and 3) on-chip automation results in reduced user interaction. While modular microfluidic IEF and PAGE approaches have been extensively explored in the literature (see J. Wu and J. Pawliszyn, *Electrophoresis*, 1993, v.14(1): pp. 469-474; J. Han and A. K. Singh, *Journal of Chromatography A*, 2004, v1049(1-2): pp. 205-209; and W. Tan, Z. H. Fan, C. X. Qui, A. J. Ricco, and I. Gibbons, *Electrophoresis* 2002, v.23(20): pp. 3638-3645), synchronized "on-chip" integration of the two schemes remains elusive (see A. E. Herr, J. I. Molho, K. A. Drouvalakis, J. C. Mikkelsen, P. J. Utz, J. G. Santiago, and T. W. Kenny, *Analytical Chemistry*, 2003, v.75(5): pp. 1180-1187; C. A. Emrich, I. L. Medintz, W. K. Chu, and R. A. Mathies, *Analytical Chemistry*, 2007, v.79 (19): pp. 7360-7366; C. Das, J. Zhang, N. D. Denslow, and Z. H. Fan, *Lab on a Chip* 2007, v.7(12): pp. 1806-1812; and J. Liu, S. Yang, C. S. Lee, and D. L. DeVoe, *Electrophoresis* 2008, v.29(11): pp. 2241-2250).

One of the primary limitations for this integration is the effect of diffusion on band resolution within the free-solution IEF stage. While polyacrylamide IPG strips are used for conventional 2-D separations, immobilizing a pH gradient on a microfluidic device is a considerable challenge. Another significant challenge involves transferring the focused bands from the liquid phase to a gel for the secondary separation. Here, we disclose high-resolution, rapid, fully-automated microfluidic platforms for achieving 2-D separations. We recently demonstrated a technique for photopolymerizing precise and well-controlled microscale immobilized pH gradients on-chip (U.S. patent application Ser. No. 12/182,755, herein incorporated by reference: and G. J. Sommer, A. K. Singh, and A. V. Hatch., *Analytical Chemistry*, 2008, v.80(9): pp. 3327-3333). This publication represented the first successful implementation of IPG methodology onto a microchip, of which we are aware, which also provided resolving power comparable to that of macroscale IPG strips. Moreover, we have also recently provided a method for fabricating microscale isoelectric fractionation (uIEF) membranes as disclosed in commonly-owned, co-pending U.S. patent application Ser. No. 12/243,817, also herein incorporated by reference in its entirety. The device presented herein, therefore, can be fabricated to use either continuous μIPG gels, or the microscale isoelectric fractionation (μIEF) membranes we have also previously disclosed for the first dimension to yield an all-gel 2-D separation microdevice, and thus enabling simpler separations with higher resolution over similar devices reported in the literature.

SUMMARY

It is, therefore, an object of this invention to provide a simple method for providing a 2-D separation of molecular species in a continuous, all-gel format without the need for handling gel strips.

It is another object of this invention to provide a 2-D separation method wherein the two dimensions are orthogonal.

It is yet another object of this invention where the two separation dimensions comprise polyacrylamide gel electrophoresis (PAGE) and isoelectric focusing (IEF).

It is still another object of this invention to provide a 2-D separation device such that sodium dodecyl sulfate (SDS) can be introduced into and incubated with focused bands in an IEF stage, enabling SDS-PAGE in the second dimension.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

BRIEF DESCRIPTION OF THE DRAWINGS

The drawings are only for the purpose of illustrating one or more preferred embodiments of the invention and are not to be construed as limiting the invention. In the drawings:

FIG. 2B shows the completion of the IEF stage illustrated in FIG. 2A, wherein the electric field is switched across the intersecting side microchannels and the focused bands are further separated by PAGE based on molecular weight.

FIG. 4A shows a close-up view of a size exclusion membrane disposed in one of the second dimension (PAGE) microchannels just below an intersecting second loading and separation microchannel.

DETAILED DESCRIPTION OF EMBODIMENTS OF THE INVENTION

Figure 1A:
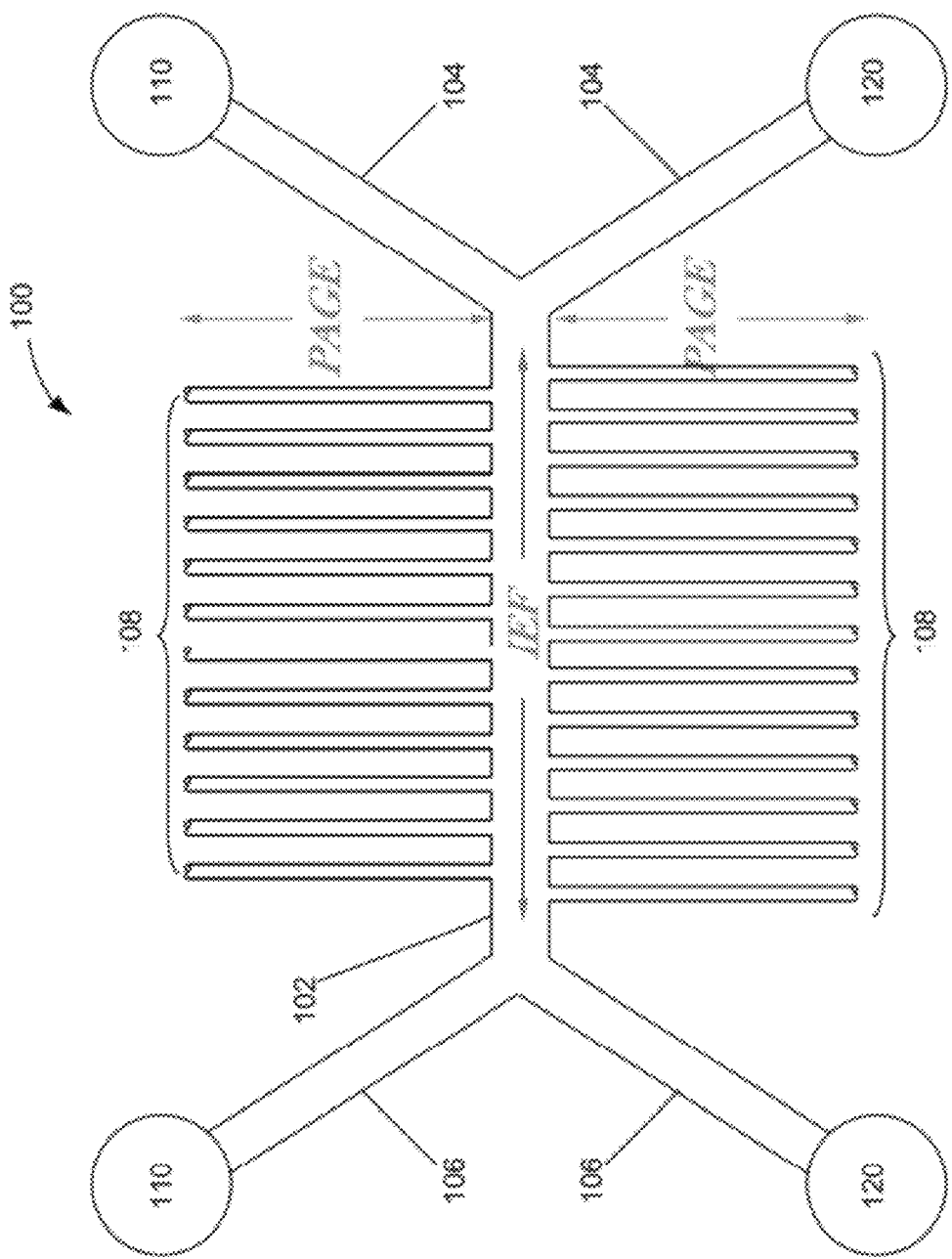
FIG. 1A illustrates a schematic of the microfluidic device geometry of the present invention.

The microchannel configuration of the present device 100 is depicted below in FIGS. 1A and 1B. The 2-D geometry is etched into a glass microchip substrate using standard lithography techniques. The general chip geometry is shown in FIG. 1A and is comprised of a central microchannel 102, having two canted or "flanking" loading microchannels 104, 106, located at either end of central microchannel 102, and a plurality of smaller side microchannels 108, each intersecting central microchannel 102 along its length and opening into it. Furthermore, while only reservoirs 110 and 120 are associated with central microchannel 102 are shown, each of side microchannels 108 is also connected with a similar reservoir (not shown) to enable convenient introduction of reagents and test samples. Additionally, devices can be made such that each set of intersecting side microchannels on either side of the central microchannel are supplied by the same reservoir, such that an equivalent electric field is distributed within each of these microchannels. Moreover, all of the microchannels are filled with a polymerized gel or buffered gel solution such that the microchannels and reservoirs are maintained in fluid communication. Finally, electrodes (not shown) are introduced into each of the microchannel reservoirs in order to provide electrical connection/communication between each of microchannels across the device.

In order to prepare these devices, microchannels are formed into a substrate material such as glass. Further, because each of the microchannels is designed to receive a polymerizable gel, each is first functionalized with an acrylate coating in order to facilitate covalent attachment of the acrylamide solution to the microchannel surfaces as the solution is polymerized. Embodiments of this dimension could also employ non-crosslinked acrylamide solutions which are not polymerized and therefore do not covalently bond to the microchannel surfaces. This polymerized gel then provides the porous medium through which an analyte-containing sample liquid is passed for separation and analysis. In the present invention these gels are configured to provide separation by means of isoelectric focusing (IEF) and by gel electrophoresis (PAGE): two analysis techniques that are independent and unrelated and are, therefore, said to be "orthogonal".

The IEF and PAGE gels are polymerized in two steps using in situ photopolymerization techniques we have previously described and now adapted for the current embodiments. In particular, the device is first filled with a suitable acrylamide base solution and an immobilized pH gradient (IPG) established along the length of the central microchannel using the diffusion-induced gradient generation procedure previously described in commonly owned, co-pending U.S. patent application Ser. No. 12/182,755, and herein incorporated by reference and as described below.

Formation of the Microscale IPG Gradient

The glass (fused silica) microchips used herein were designed in-house and fabricated by Caliper Life Sciences (Hopkinton, Mass.) using standard wet etching techniques. The microchannel configuration of the microchip is shown schematically in FIG. 1A. The IEF stage includes central microchannel 102, flanking loading microchannels 104 and 106 and reservoirs 110 and 120. The microchannels are all approximately 25 μm deep, by approximately 100 μm wide and disposed in a modified "H" geometry. Moreover, central microchannel 102 is used to hold and support the gradient of molecular species (IPG) and is in fluid communication wiih the two sets of pair of flanking loading microchannels 104 and 106 and reservoirs 110 and 120. To ensure covalent bonding between the acrylamide solution and the walls of the microchannels once the solution is polymerized, the microchannels were coated with an acrylate-terminated coating. The acrylaie-terminated coating is established by first cleaning the microchannel interior walls by flooding the microchannels with a IM aqueous NaOH solution for a short period and then rinsing the microchannels with a quantity of deionized water, after which the microchip was dried thoroughly in a vacuum. While the microchip was cleaned, a 2:3:5 (v/v/v) solution mixture of 3-(Trimethoxysilyl)propyl melhacrylate, glacial acetic acid, and deionized water was prepared, sonicated, and degassed. This solution mixture was then loaded into the microchannels of the microchip where it was allowed to react with the interior microchannel walls for 30 minutes at room temperature. The solution mixture was then flushed out of the microchannels, rinsed a first time with a 3:7 (v/v) mixture of acetic acid and water, rinsed a second time with deionized water, and thoroughly dried as before in a vacuum. This treatment provides an interior wall surface comprising a plurality of acrylale functionalities to which the subsequently introduced acrylamide solution will be bonded upon polymerization.

After the foregoing surface treatment, the center microchannel of the microchip was loaded with a degassed solution comprising 10% T, 2.6% C acrylamide/bisacrylamide with 0.2% (w/v) of the water soluble VA-086 photoinitiator, 2,2'-azobis[2-methyl-N-(2-hydroxyethyl)propionamide (obtained from Wako Chemicals, USA, Inc., Richmond, Va.). As used herein, "T", is expressed as a percentage of the total weight of acrylamide plus bisacrylamide used to form a desired volume of acrylamide solution. Thus, a T of 1.0% would indicate that there is a total of 10 grams of acrylamide plus bisacrylamide per 100 ml of solution, i.e., $$\% \; T(\text{total}) = \frac{g(\text{acryl} + \text{bis})}{100 \; ml}.$$

Furthermore, "C" is expressed as a percentage of the weight of bisacrylamide (crosslinker) to the total weight of the acrylamide plus bisacrylamide, i.e.

$$\% \; C = \frac{g(\text{bis})}{100 \; g(\text{acryl} + \text{bis})}$$

Figure 2A:
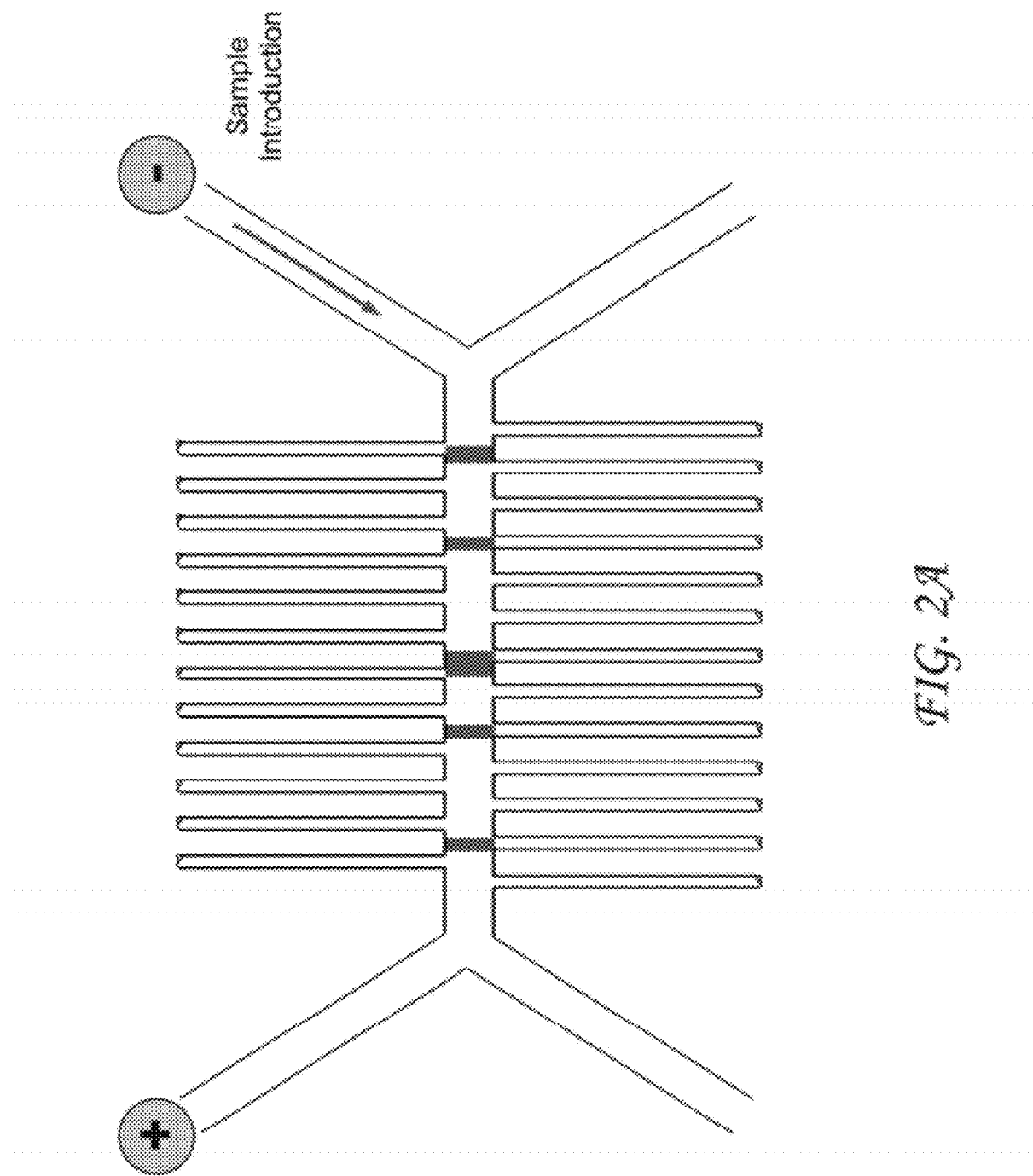
FIG. 2A shows the 2-dimensional separation operation of the present device, wherein samples are introduced along one of the flanking microchannels and driven into the IPG, enabling separation based on isoelectric point.

Two solutions of the four shown in TABLE I below were prepared by first mixing the constituents listed in the recipe and then sonicating and degassing the mixture. In particular, a first solution comprising the higher 7.0 pH solution and a second comprising the lower 3.8 pH solution were prepared from 5% T, 2.6% C acrylamide/bisacrylamide, mixed with 0.2% (w/v) VA-086 photoinitiator with calculated amounts of the IMMOBILINE® acrylamido buffers identified in TABLE 1. 2 μL of each solution was loaded into reservoir holes (not shown) associated with flanking microchannels 104 and 106 on either side of central microchannel 102 as shown in FIG. 2A. The microchip was then loaded into a custom manifold (not shown), allowing simple attachment of cylindrical plastic 200 μL pipette tips to each of reservoirs 110 and 120. The reservoirs on either side of the center microchannel were then loaded with the T+C monomer/IMMOBILINE® acrylamido buffers/photoinitiator solutions of different pH so as to induce continuous flow along the flanking microchannels adjacent to the center microchannel.

TABLE 1

| Reagent | pH 3.8 solution | pH 5.0 solution | pH 6.0 solution | pH 7.0 solution |
|---|---|---|---|---|
| Acrylamide/Bisacrylamide | 5% T, 2.6% C | 5% T, 2.6% C | 5% T, 2.6% C | 5% T, 2.6% C |
| IMMOBILINE ® acrylamido buffer - pK 3.6 | 12.7 mM | 8.98 mM | 6.68 mM | 4.4 mM |
| IMMOBILINE ® acrylamido buffer - pK 4.6 | — | 3.86 mM | 7.08 mM | 10.3 mM |
| IMMOBILINE ® acrylamido buffer - pK 6.2 | 7.48 mM | 5.56 mM | 3.96 mM | 2.36 mM |
| IMMOBILINE ® acrylamido buffer - pK 7.0 | — | 1.56 mM | 2.87 mM | 4.17 mM |
| IMMOBILINE ® acrylamido buffer - pK 9.3 | — | 4.85 mM | 8.43 mM | 12.1 mM |
| VA-086 photoinitiator | 0.2% (w/v) | 0.2% (w/v) | 0.2% (w/v) | 0.2% (w/v) |

Recipes for fabricating pH 3.8-7.0 μIPG

Once the device reservoirs have been loaded with solution the gradient is allowed to form by placing the microdevice in a damp, dark environment for a sufficient time period to allow linear equilibration of the IMMOBILINE® acrylamido buffers across the center microchannel. Devices were typically equilibrated overnight for 16 hours to ensure linear distributions.

Following equilibration the excess solution in each if the reservoirs was removed and the entire microchip was masked and then exposed to light from a 100-W 365-nm lamp for 8 minutes to photopolymerize the solution within the center microchannel. The excess unpolymerized solution in each via was then removed and the chip was stored in deionized water until needed. Note that the polymerized gel must remain hydrated since the gel becomes defective upon dehydration.

The photomask was used to prevent polymerization within the adjacent intersecting side microchannels intended for PAGE analysis.

Formation of the PAGE Array

After central microchannel 102 was polymerized, the unpolymerized acrylamide solution within the two arrays of side microchannels 108 on either side of the central microchannel was drained and replaced with a 6% T polyacrylamide solution and the solution photopolymerized in the same manner described above. It will be appreciated that while 6% T is disclosed herein for use in the side microchannel array, other acrylamide mixtures are also possible and likely. The 6% T polyacrylamide portion of the device could be made with a range of different compositions: anywhere from 3%-20% T, depending on the type and natures of the analytes being studied. Moreover, one could also fabricate gels having a gradient in porosity in this region, such as a linear 5%-40% gradient, along the lengths of each of the intersecting side microchannels comprising the second dimension. The side microchannels could also be filled with a non-crosslinked acrylamide solution. In all cases the device is stored in a buffer solution for later use.

By forming the device in this manner an integrated, all-gel separation device is prepared.

Device Operation

Two-dimensional separation is achieved in the device described above by using the electrophoretic manipulation shown schematically in FIGS. 2A and 2B. Samples are initially introduced through one of the reservoirs attached to ends of the flanking loading microchannels attached to the central separation microchannel. The sample is driven into the TPG disposed within central microchannel by applying an electromotive force, in this case a voltage potential, generated by an electrical power supply (not shown) attached to electrodes (depicted as "+" and "−" in FIG. 2A) inserted into the reservoirs 110. Species may be diluted in a buffer suitable for IEF separation. The buffer may keep species in their native state, or include additives that reduce or denature species. Possible additives include, but are not limited to, urea, thiourea, CHAPS, Tween-20, and dithiothreitol. Analyte species within the introduced sample migrate through the IPG toward their respective pI points 202 along the pH gradient and are "focused" at these relative locations. Sample loading continues until the desired species (e.g. protein) concentrations are reached as determined through either visual inspection or through calibrated loading voltages and times based on expected sample mobilities and concentrations. Note that concentrations are controlled by switching from loading sample from the sample reservoir 110 to loading buffer solution from buffer reservoirs 120 and vice versa.

Following the IEF separation, the focused bands are driven orthogonally into the PAGE microchannels by switching the electric field across those microchannels. Due to differences in molecular weight, species elute at different rates enabling further separation ("fractionation") 204 as shown schematically in FIG. 2R.

Figure 1B:
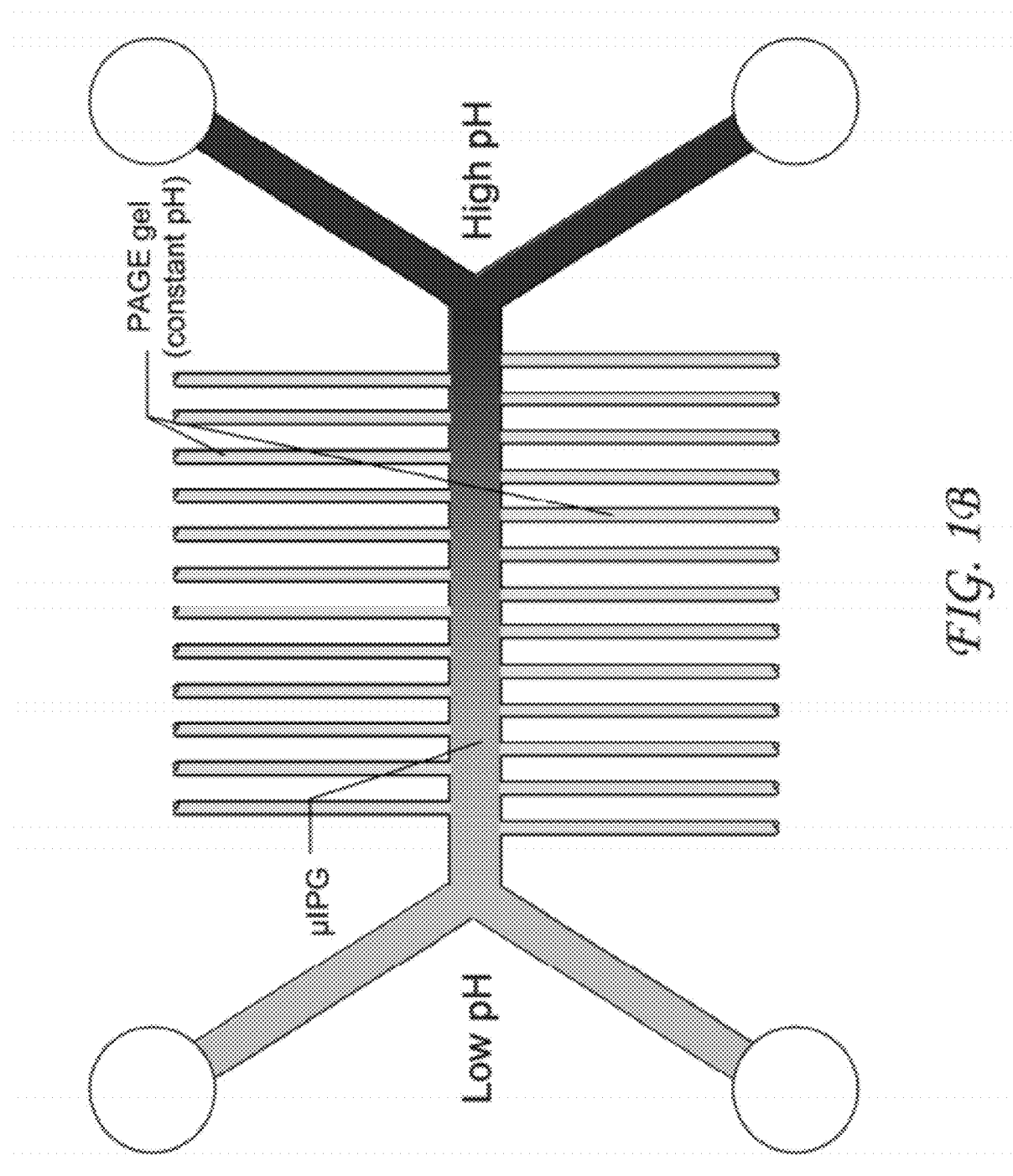
FIG. 1B illustrates a device fabricated such that an immobilized polyacrylamide gel (IPG) is incorporated and polymerized along a central microchannel and a plurality of intersecting side microchannels each containing a cross-linked polymerized gel having a constant pH throughout.

In a variation of the embodiment shown in FIG. 1B, the device can be further modified such that it enables loading of a sodium dodecyl sulfate (SDS) solution into the IPG stage following the IEF step. SDS incubation is typically done following IEF to achieve higher resolution in the second dimension since SDS equilibrates the mass/charge ratio for all proteins. However, in order to provide a structure for the SDS step a portion of central channel 102 must remain open along its length and free of the IPG gel to allow access for introducing the SDS solution into the separation structure.

Figure 3:
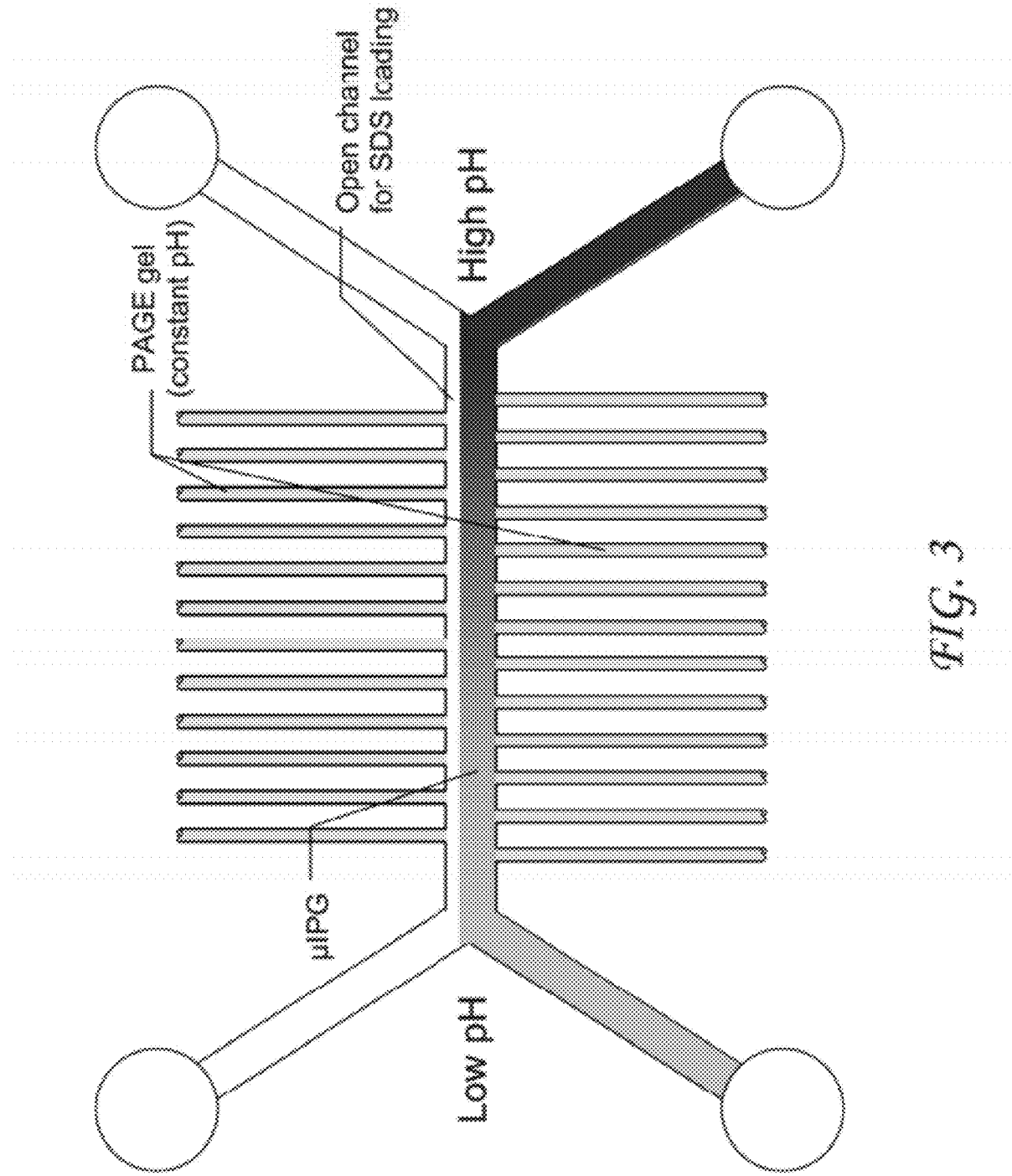
FIG. 3 shows a modified 2-dimensional system in which a portion of the central microchannel is left open such that SDS can be loaded following IEF separation and diffused into focused bands within the IPG. SDS incubation provides a constant charge-to-mass ratio to protein samples, and thus provides for higher resolution in the second dimension (PAGE).

This embodiment, therefore, is provided by first preparing the IPG phase (the T+C monomer/IMMOBILINE® acrylamido buffers/photoinitiator solutions) and introducing the solutions into central microchannel 102 as before, but instead of polymerizing the entire volume of microchannel a portion of the width (depth) of the microchannel along its length is masked to prevent photopolymerizing the entire cross-section of the gel when forming the IPG. In this way only a portion of the acrylamide solution filling the central microchannel width (or depth) is polymerized while leaving the remaining portion of the acrylamide solution unpolymerized and unattached to the interior walls of the central microchannel. After preparing the IPG in this manner, the device is rinsed to wash the unpolymerized portion of the gel from the central microchannel. What remains is the structure shown in FIG. 3 having a void space running along the length of central microchannel 102 from end-to-end, spanning approximately half of the width (depth) and having a generally uniform cross-sectional area.

After electrophoretically loading and focusing an analyte sample into the porous IPG polymer as described above, a quantity of the SDS solution is introduced into the open portion of the central microchannel such that the SDS diffuses into the IPG and treats the focused bands such that each can be readily separated in the second dimension, i.e., the PAGE separation stage. After 5-10 minutes of incubation, the second dimension PAGE separation is initiated and conducted as previously described, except that the proteins are now SDS-denatured (SDS-PAGE) rather than in the state required for IEF separation.

Figure 4B:
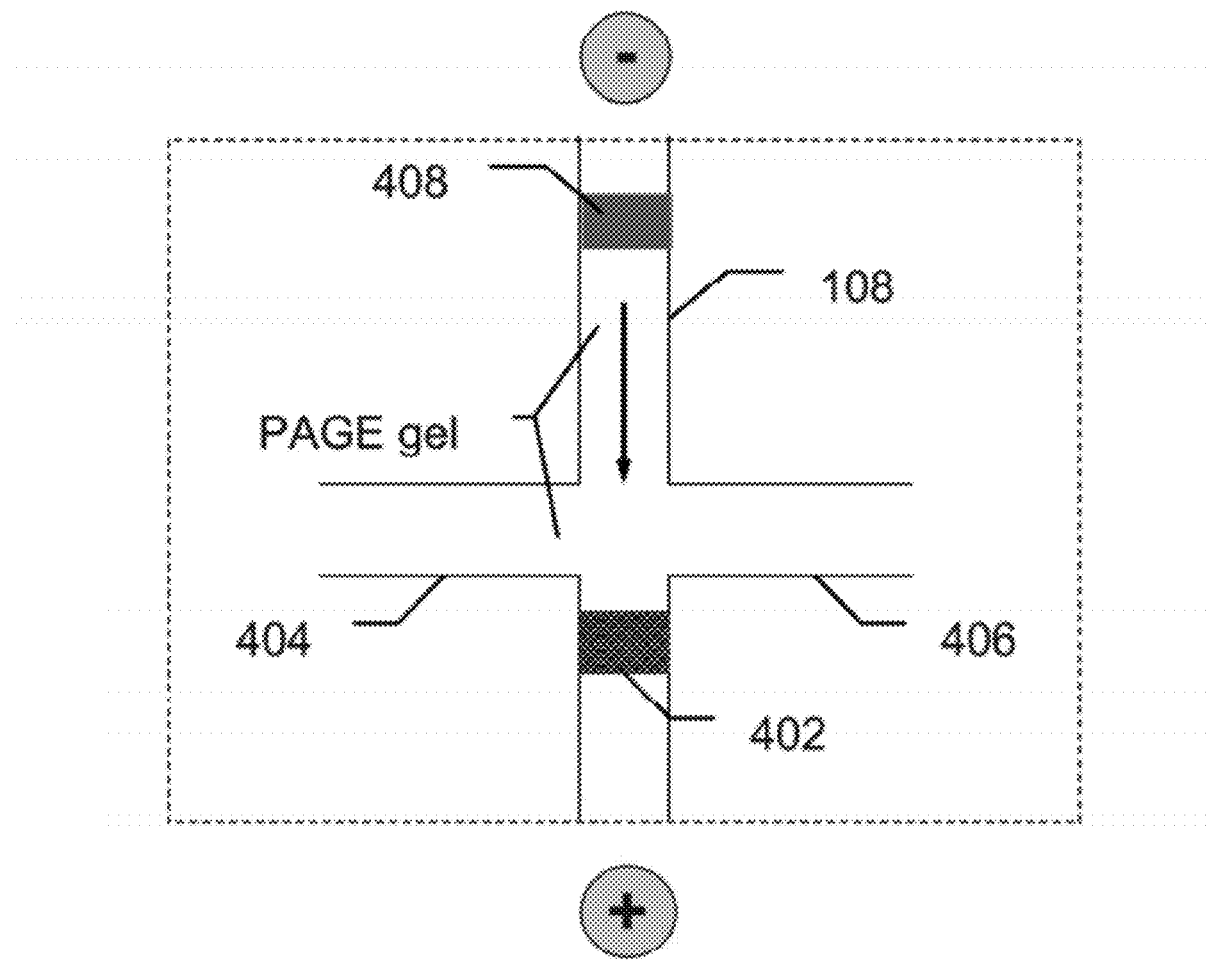
FIG. 4B shows a close-up view of the size exclusion membrane disposed in one of the second dimension (PAGE) microchannels just below an auxiliary intersecting loading and separation microchannel.

Again, further modification is also possible as a second embodiment of the SDS-PAGE process using the device of the present invention. In particular, SDS can be incorporated in the second dimension by using an adaptation such as that shown schematically in FIGS. 4A-4B and FIGS. 5A-5D. Here, a sample analyte has been loaded into the microfluidic separation device 100 as shown in FIG. 4A and focused into bands in a first dimension and then transferred as bands 408 in the second dimension as described above. In this current embodiment, device 100 further includes a porous polymer size-exclusion membrane 402, such as those that we have previously described in U.S. patent application Ser. Nos. 12/182,755 and 12/243,817, herein incorporated by reference, that are useful for preconcentration and size-based fractionation. Membrane 402 is disposed within one or more of the side microchannels 108. Intersecting microchannels 404 and 406 are included just ahead of membrane 402 each of which contains the same polyacrylamide gel as microchannels 108 (6% T in the present embodiment).

The size exclusion membrane 402 is formed by filling the microchannel with a acrylamide/bisacrylamide gel solution and then exposing the selected microchannel region of the microchannel to a rectangular-shaped high intensity beam for a time sufficient to photopolymerize the acrylamide/bisacrylamide solution, as shown in FIGS. 4A and 4B (a close-up view of this embodiment). In the present embodiment a membrane having a low degree of porosity is desired and an acrylamide solution mixture comprising 45% T, 12% C was, therefore, utilized. However, one could make the membrane with solutions ranging from 20% T-50% T, and 2% C-15% C. One could also fabricate a membrane with a negative charge incorporated into the matrix which also helps to exclude proteins, by using, for example, the same IMMOBILINE® acrylamido buffer solutions we use in fabricating the IPG gels and isoelectric fabrication membranes.

Figure 5A:
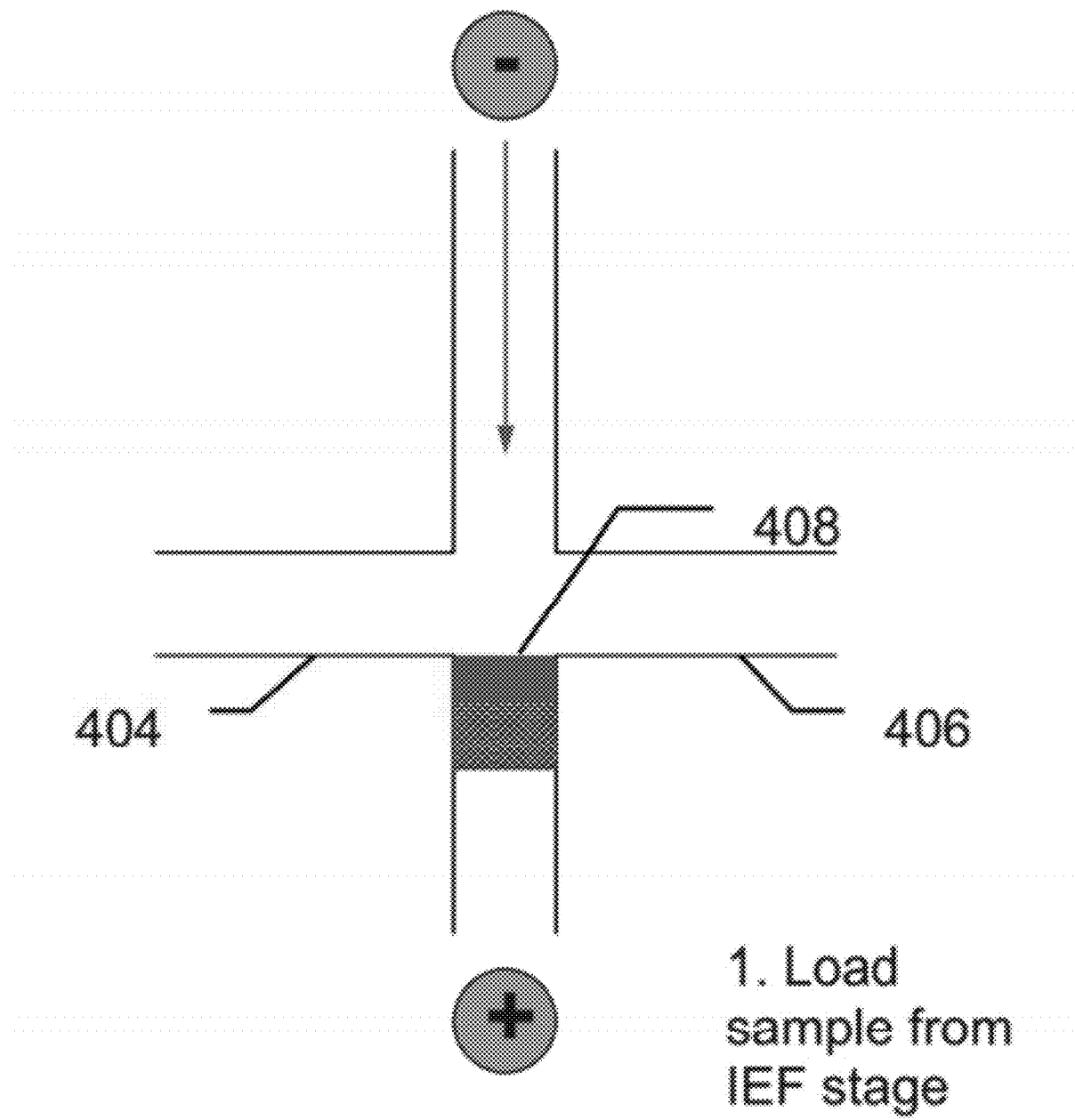
FIGS. 5A-5D show the procedure for performing SDS incubation at the size exclusion membrane within the second dimension, wherein the sample and SDS are loaded or "stacked" against the exclusion membrane in separate steps. Following stacking of the focused sample and SDS, the complex is separated along a constant pH. PAGE microchannel.

The embodiment shown in FIGS. 4A and 4B is utilized as shown in FIGS. 5A-5D. In particular, a pair of electrodes, herein depicted as "+" and is introduced and situated on either side of size exclusion membrane 402 as shown in FIG. 5A. Moreover, the electrodes are in communication with the particular microchannels 108 in which the PAGE separated analyte sample 408 is contained. Sample 408 is transported, as before, through one of the microchannels 108 (depicted by arrow) and onto of the one or more size exclusion membranes 402 by applying a constant potential electrical signal supplied by a high voltage power supply (not shown). Proteins comprising sample analyte 408, therefore, are selectively concentrated against one of porous membranes 402 while ions are free to pass through it thereby maintaining an electrical current throughout the system.

Figure 5B:
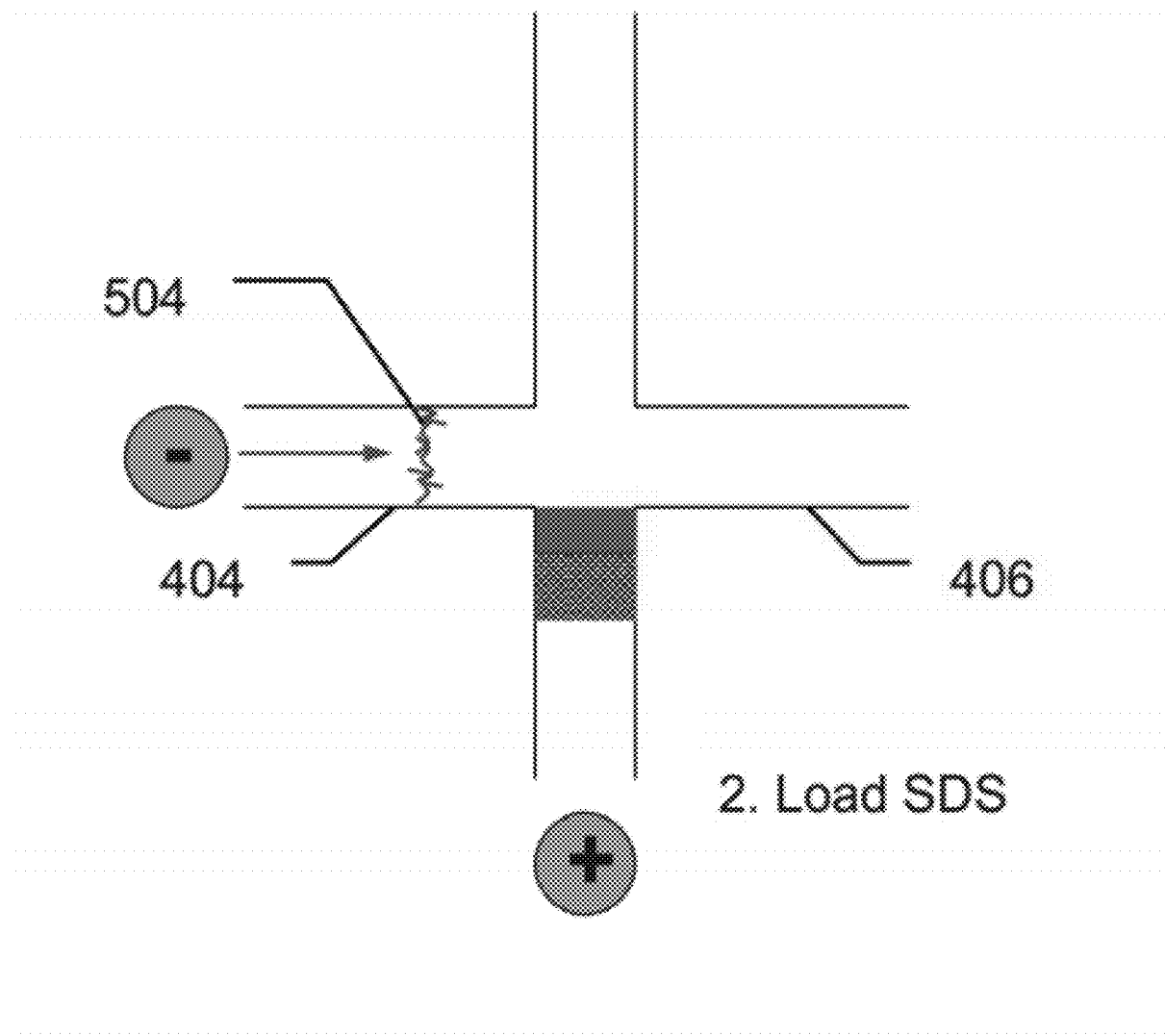

With the sample stacked against the size exclusion membranes as shown in FIG. 5B, an SDS solution 504 can then be loaded (as indicated by the arrow) into one or the other of intersecting microchannels 404 and transported to sample concentrated on the size exclusion membrane by switching the electrical potential such that an electric potential is now impressed between one of microchannels 404 and across the membrane. This allows for SDS-incubation of the sample proteins trapped at the membrane which in turn provides for treating these sample proteins prior to the SDS-PAGE separation stage.

Figure 5C:
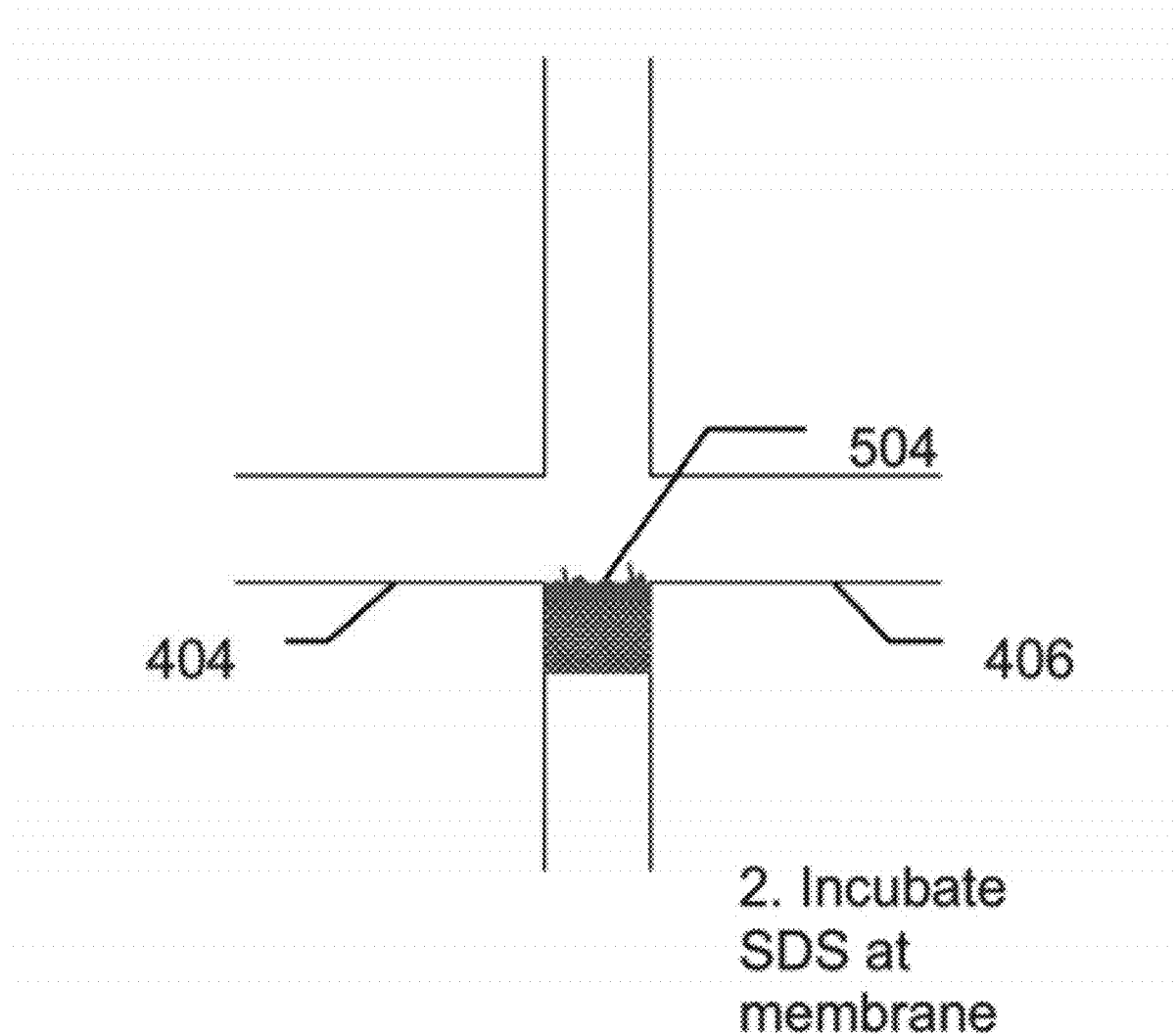

After loading the SDS onto sample 408 the sample is allowed to contact and interact with the SDS (i.e., incubate) and as shown in FIG. 5C in order to treat the proteins. While the present process incubates these proteins for 5 minutes incubation times of from 2 to 10 minutes are useful.

Figure 5D:
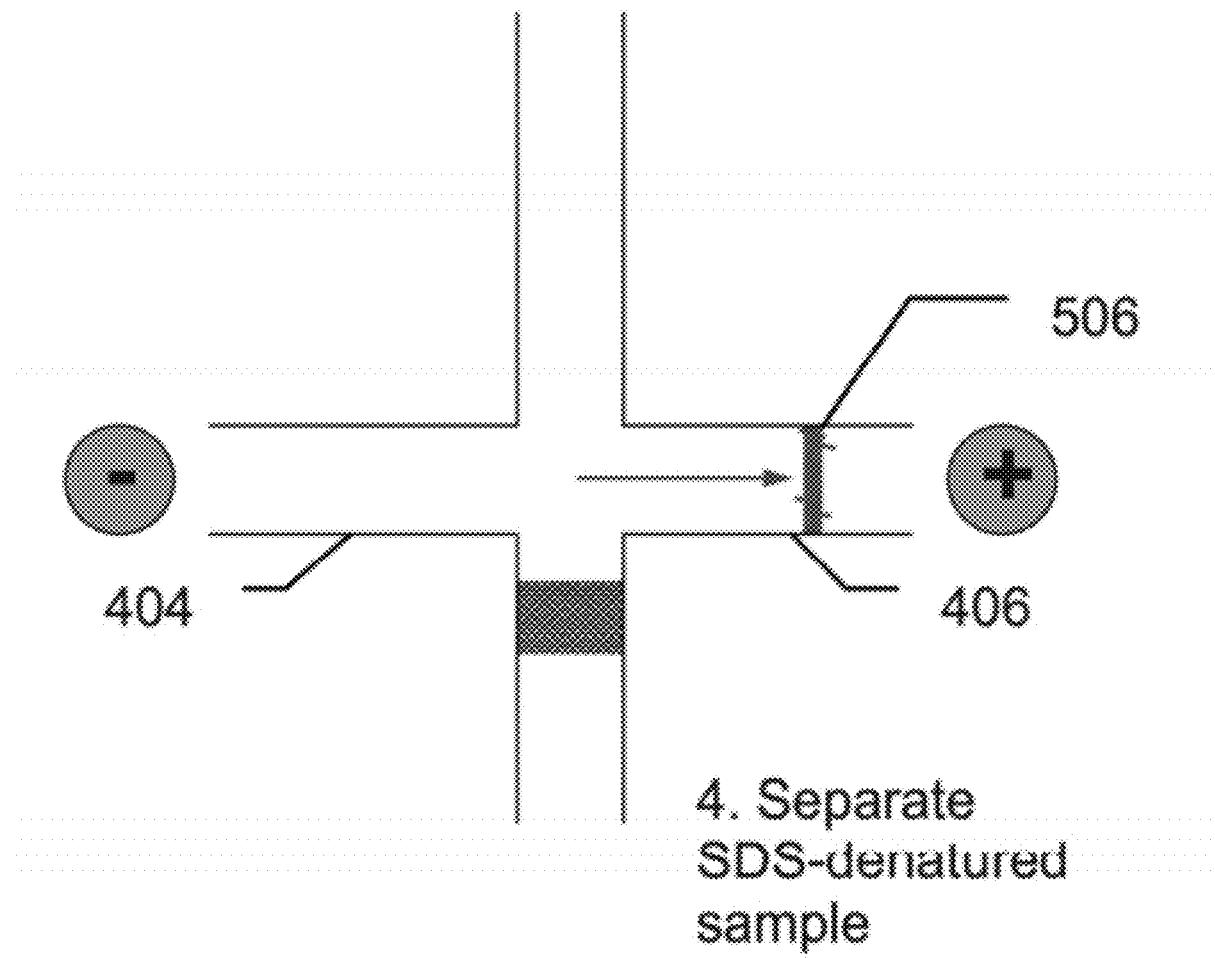

After incubation the electric potential is again power switched to electrodes disposed at either end of intersecting microchannels 404 and 406 as shown in FIG. 5D such that the SDS-denatured sample 506 is electrically transported from the size exclusion membrane for further separation (i.e., SDS-PAGE).

Figure 6:
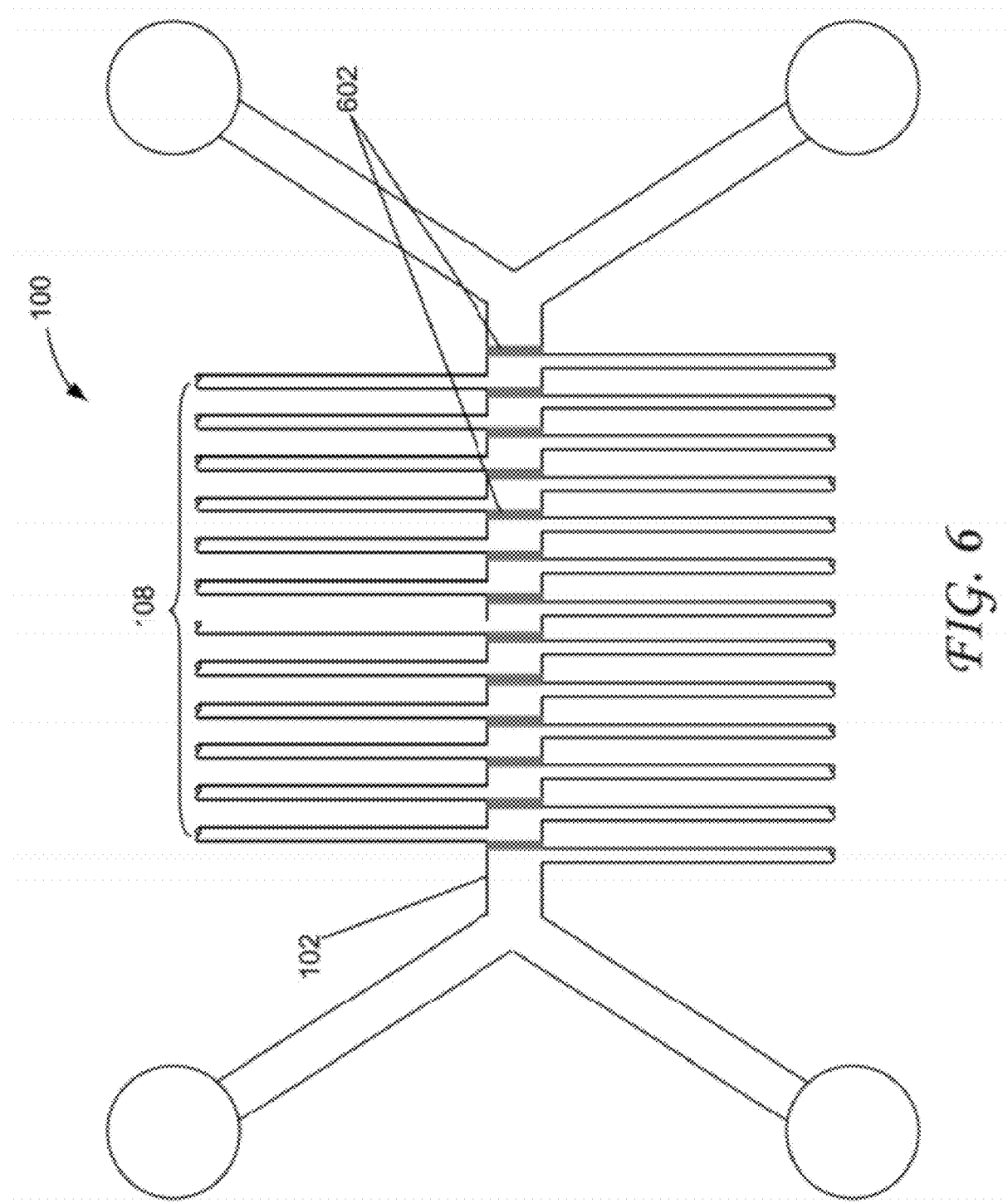
FIG. 6 shows a modified 2-dimensional system in which the center separation microchannel comprises a series of size exclusion membranes inserted at regular intervals to provide a means for improved resolution and better transfer into the second separation dimension by effectively "binning" the analyte species separated within the center first dimension IEF microchannel.

In still another embodiment, the device 100 depicted in FIG. 1A may also be fabricated to include one or more porous membranes 602 disposed along the length of microchannel 102, wherein each membrane has a unique and specific pH value such as to enable isoelectric fractionation along the first dimension, as shown in FIG. 6. These membranes provide another means for improving the resolution in the first separation dimension since the technique effectively "bins" the analyte species being separated into discrete zones based on their isoelectric point. For instance, each membrane might represent a zone of 0.2 pH units such that a first zone might contain proteins or other species having a pI spanning pH units between 6.8 and 7.0; zone 2 might contain species having a pI from 7.0 to 7.2; and so forth. That is, fractionation occurs by charged-based exclusion, not size-based exclusion.

Moreover, there is no need for using a range of porosities: each membrane in this embodiment may have identical porosity. Furthermore, the membranes of this embodiment are deliberately fabricated to be quite porous such that proteins or other species migrate through them easily if they are not constrained from further migration based on the imposing pH of the membrane. The isoelectric fractionation membranes of this embodiment are fabricated with 4% T, 10% C acrylamide/bisacrylamide but the membranes also could be fabricated with acrylamide/bisacrylamide ranging from 3-10% T and 1-12% C, respectively.

This sort of fractionation, therefore, allows for more uniform injection of each zone into the second dimension (PAGE) microchannels, and also ensures a precise pi zone being contained within each of the several second dimension microchannels. In this way the transfer of these species into the second dimension PAGE separations process is also improved.

Figure 7A:
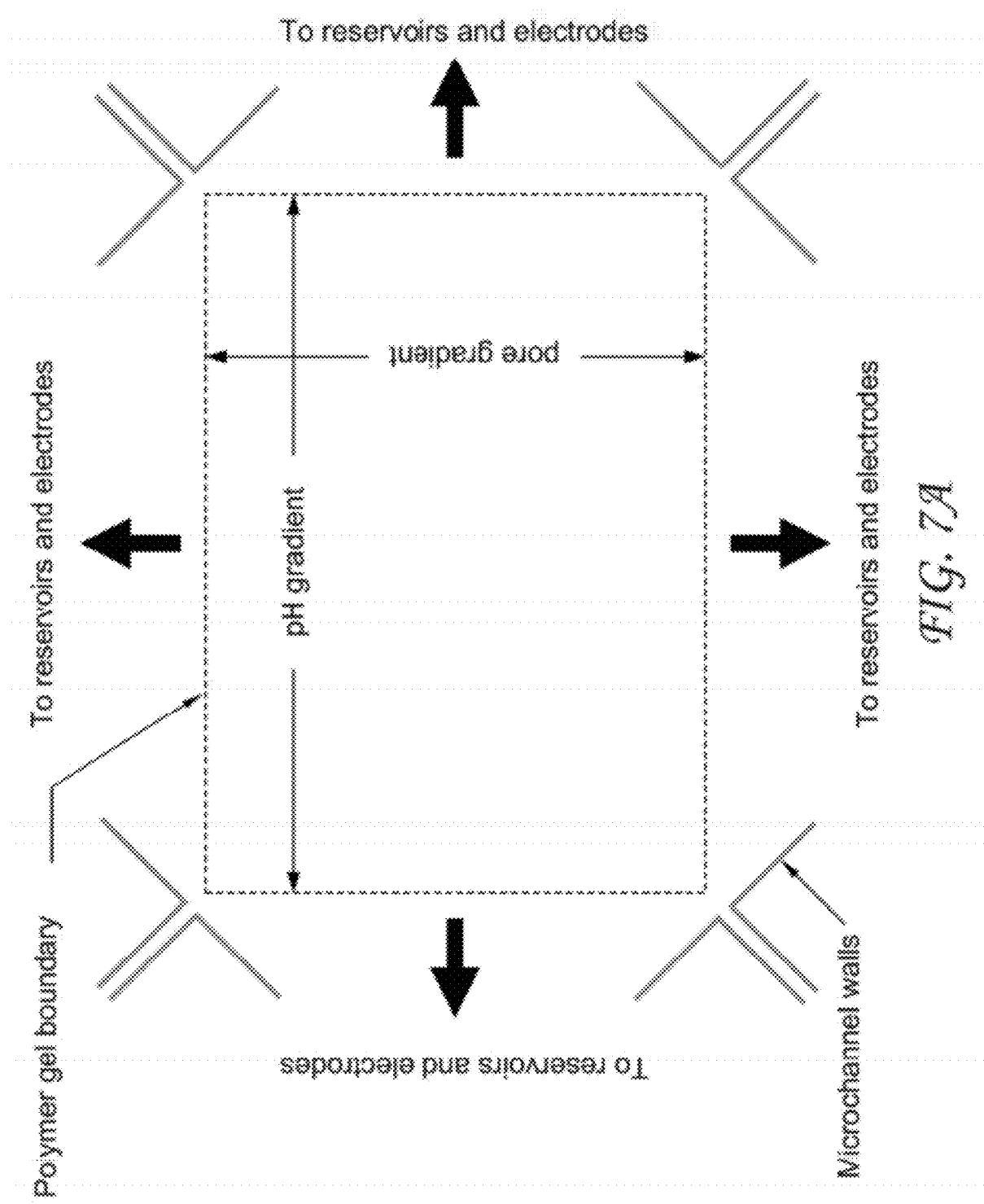
FIG. 7A shows a schematic diagram of a 2-dimensional separation device, wherein a polymer gel disposed in a single thin, central micro-volume such that an IPG is created in a first horizontal (or vertical) direction and a porosity gradient is created in a second vertical (or horizontal) direction, and wherein the central micro-volume is open to and in fluid and electrical communication with side reservoirs and electrodes in each of the four coordinate directions. Also included is a separate microchannel through which samples are introduced into the central micro-volume.
Figure 7B:
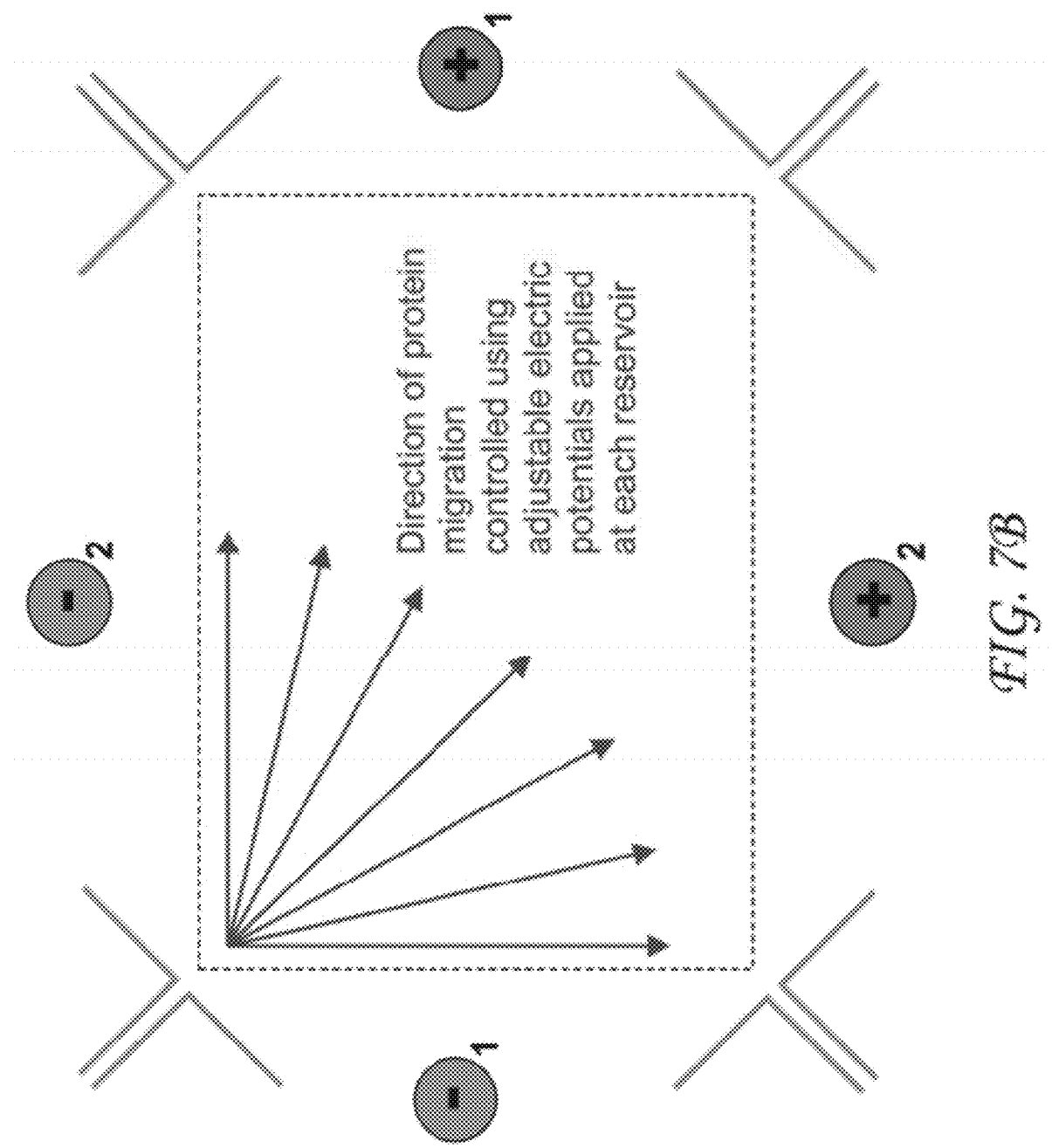
FIG. 7B diagrammatically shows the location of the electrodes used to control the direction of species (e.g. protein) migration using adjustable electric potentials applied between pairs of electrodes located in each reservoir.
Figure 7C:
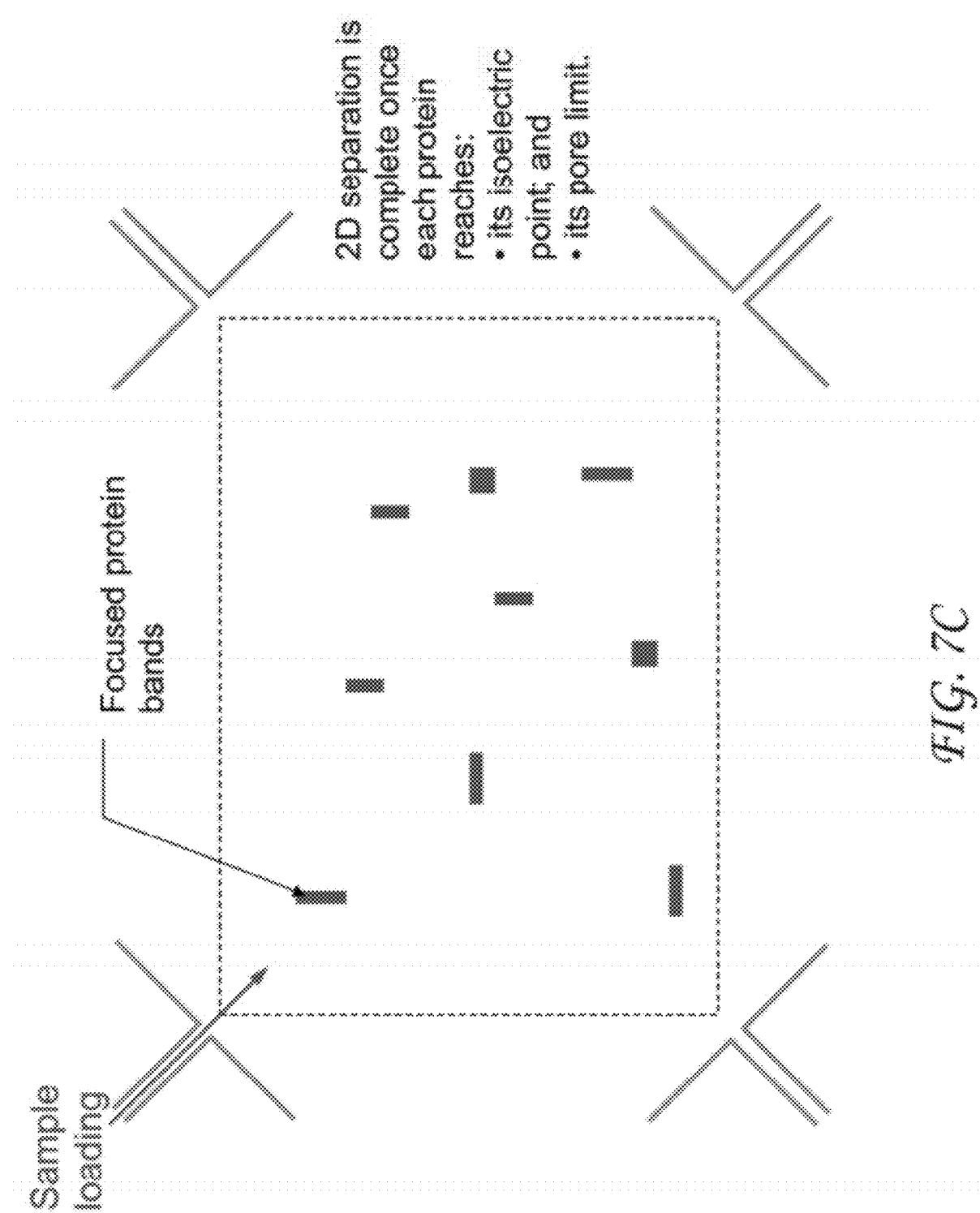
FIG. 7C schematically shows the completed result of the 2-dimensional separation operation of the present embodiment as each of the species has reached its isoelectric point and its pore limit.

Finally, a further embodiment of the present invention can be prepared as shown in the device depicted in FIGS. 7A-7C. In this embodiment, both separation dimensions are polymerized and immobilized within the same microchannel volume, such that the 2-D separation occurs simultaneously. Separation occurs via IEF in the first dimension along the horizontal direction and via pore limit electrophoresis in the second dimension along the vertical direction as shown in FIG. 7A.

This device embodiment is fabricated by first establishing and photopolymerizing an IPG within the entire gel boundary depicted in FIG. 7A using the fabrication methods described above. The IPG is photopolymerized within a porous polyacrylamide gel. Presently, the IPG is fabricated with 4% T, 2.6% C. However, the IPG may be fabricated with an acrylamide/bisacrylamide solution ranging from 2-8% T and 1-10% C. The pH gradient is prepared as previously described and in U.S. patent application Ser. Nos. 12/182,755 and 12/243,817, from one side to the opposite side of the device shown in FIG. 7A after which the solution is photopolymerized as before.

Next, a porosity gradient is immobilized in the second dimension across the same gel boundary using a fabrication technique adapted from that described in U.S. patent application Ser. No. 12/182,755. To accomplish this a second pair of acrylamide/bisacrylamide solutions, each having a different % T and/or % C composition is prepared. In the current embodiment, solutions consisting of 4% T, 2.6% C and 40% T, 12% C are prepared; however, devices can be prepared with solutions ranging from 2% T, 1% C to 45% T, 15% C. Quantities of each of these compositions are then introduced into the device such that the lower percentage solution (i.e., 4% T, 2.6% C) flows adjacent to the top of the gel boundary, and the higher percentage solution (i.e., 40%T, 12%C) flows adjacent to the bottom of the gel boundary shown in FIG. 7A In this manner a gradient in acrylamide Disacrylamide concentration is established via diffusion across the porous IPG gel orthogonal to the pH gradient. The entire gel boundary area is then nhotonolvmerized auain to immobilize the oorositv gradient within the porous IPG.

The embodiment of FIGS. 7A-7C is utilized by electrophoretically loading samples into the gel boundary area by controlling electric potentials applied across the gel boundary area through electrodes contacting the fluidically connected device reservoirs shown in FIG. 7B. Electrode potentials applied to each side of the gel boundary area can be adjusted to control the direction of sample migration through the gel boundary area. Presently, the electric potentials are first set such that samples migrate across the first (horizontal) dimension and then transitioned to enable migration along the second (vertical) dimension. Each focused protein band will eventually stop migration in both directions as shown in FIG. 7C as it approaches: a) its isoelectric point, then b) its pore limit—the porosity at which a protein no longer migrates due to size-based exclusion of the gel.

We have disclosed, therefore, several embodiments of a device and associated techniques for achieving 2-D separations within an integrated microdevice. Separation mechanisms we have previously disclosed are incorporated with a PAGE gel mechanism as a second orthogonal dimension within a fully-automated microfluidic platform. This technique enables higher resolution over existing 2-D microdevices due to the decreased dispersive effects and inter-diffusion between dimensions achieved with an all-gel device.

Thus having described exemplary embodiments of the present invention, it should be noted by those skilled in the art that the disclosures herein are exemplary only and that various other alternatives, adaptations, and modifications may be made within the scope of the present invention. Accordingly, the present invention is not limited to the specific embodiments as illustrated herein, but is only limited by the following claims.

Finally, to the extent necessary to understand or complete the disclosure of the present invention, all publications, patents, and patent applications mentioned herein are expressly incorporated by reference therein to the same extent as though each were individually so incorporated.

What is claimed is:

1. A two-dimensional (2-D) microchannel separation device, comprising:
an isoelectric focusing (IEF) stage in electrical and fluid communication with an orthogonal polyacrylamide electrophoretic gel (PAGE) separation stage, wherein the IEF stage comprises a central microchannel having a first end and a second end, the microchannel including one or more interior surfaces with an acrylate-terminated coating covalently bonded thereto, and an immobilized pH gradient polymer gel covalently bonded to the acrylate-terminated coating, and wherein the polymer gel only partially fills the central microchannel, the unfilled microchannel space having a generally uniform cross-sectional area between the first and second ends;
electrode disposed at each of a first and a second end of the IEF stage and at each of a first and a second end of the PAGE stage;
a power supply in electrical communication with each of the electrodes; and switching means for applying an electric potential between any two of the electrodes.

2. The 2-D microchannel separation device of claim 1, wherein the immobilized pH gradient polymer gel comprises a polymerized acrylamide/bisacrylamide solution comprising a plurality of preselected acrylamido buffers having different pK values distributed within the acrylamide/bisacrylamide solution to provide a gradient in pH values from the first end to the second end of the central microchannel.

3. The 2-D microchannel separation device of claim 1, wherein the orthogonal PAGE separation stage comprises one or more intersecting side microchannels each comprising a length, width and depth, one or more interior surfaces comprising an acrylate-terminated coating covalently bonded thereto, and a polymerized acrylamide gel disposed within and filling the one or more microchannels and covalently bonded to the acrylate-terminated coating, wherein each of the intersecting side microchannels is in electrical and fluid communication with the central microchannel.

4. The 2-D microchannel separation device of claim 3, wherein the orthogonal PAGE separation stage comprises a plurality of intersecting side microchannels disposed along the length of the central microchannel.

5. The 2-D microchannel separation device of claim 4, wherein the PAGE separation stage comprises one or more size exclusion membranes spanning the width/depth of a short portion of the length of one or more of the plurality of intersecting side microchannels, and one or more secondary microchannel disposed between the central microchannel and the size exclusion membrane and intersecting each of the one or more intersecting side microchannels adjacent to the size exclusion membrane.

6. The 2-D microchannel separation device of claim 5, wherein the IEF stage comprises one or more focused bands each comprising a different species and a means for treating each species in situ prior to the PAGE separation stage.

7. The 2-D microchannel separation device of claim 6, wherein the means for treating comprises a quantity of sodium dodecyl sulfate (SDS) introduced in the presence of the one or more focused bands.

8. The 2-D microchannel separation device of claim 1, wherein the orthogonal PAGE separation stage comprises a plurality of intersecting side microchannels disposed along the length of the central microchannel.

9. The 2-D microchannel separation device of claim 8, wherein the PAGE separation stage comprises one or more size exclusion membranes spanning the width/depth of a short portion of the length of one or more of the plurality of intersecting side microchannels, and one or more secondary microchannel disposed between the central microchannel and the size exclusion membrane and intersecting each of the one or more intersecting side microchannels adjacent to the size exclusion membrane.

10. The 2-D microchannel separation device of claim 9, wherein the IEF stage comprises one or more focused bands each comprising a different species and a means for treating each species in situ prior to the PAGE separation stage.

11. The 2-D microchannel separation device of claim 10, wherein the means for treating comprises a quantity of sodium dodecyl sulfate (SDS) introduced in the presence of the one or more focused bands.

12. The 2-D microchannel separation device of claim 1, wherein the IEF stage comprises a central microchannel having a length and cross-section, one or more interior surfaces comprising an acrylate-terminated coating covalently bonded thereto, and a plurality of porous membranes covalently bonded to the acrylate-terminated coating each spanning the central microchannel cross-section, wherein the plurality of porous membranes are disposed at intervals along the length of the central microchannel and wherein each comprises a specific pH.

13. The 2-D microchannel separation device of claim 12, wherein the porous membranes comprise a polymerized acrylamide/bisacrylamide gel, wherein the acrylamide/bisacrylamide gel comprises a composition range of 3-10% T and 1-12% C, and wherein a plurality of preselected acrylamido buffers having different pK values are disposed within the acrylamide/bisacrylamide gel to impose a specific pH within the porous membrane.

14. The 2-D microchannel separation device of claim 1, wherein the IEF stage and the orthogonal PAGE stage comprise a single polymerized polyacrylamide gel disposed within a central micro-volume, the polymerized gel having a length extending from a first end to a second end of the central micro-volume, and a width extending from a third end to a fourth end of the central micro-volume, wherein the IEF stage comprises a continuous immobilized pH gradient extending across the length of the central micro-volume, and wherein the orthogonal PAGE stage comprises a gradient in porosity extending across the width of the central micro-volume.

15. The 2-D microchannel separation device of claim 14, wherein the IEF stage comprises a plurality of preselected acrylamido buffer solutions each having different pK values distributed within the acrylamide/bisacrylamide gel to provide a gradient in pH values from the first end to the second end of the central micro-volume, and wherein the PAGE stage comprises a distribution of acrylamide monomer and bisacrylamide crosslinker to provide a gradient in porosity from the third end to the fourth end of the central micro-volume.

* * * * *